(12) United States Patent
Yang

(10) Patent No.: US 10,706,594 B2
(45) Date of Patent: *Jul. 7, 2020

(54) SYSTEMS AND METHODS FOR IMAGE DATA PROCESSING IN COMPUTERIZED TOMOGRAPHY

(71) Applicant: SHANGHAI UNITED IMAGING HEALTHCARE CO., LTD., Shanghai (CN)

(72) Inventor: Yao Yang, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 0 days.

This patent is subject to a terminal disclaimer.

(21) Appl. No.: 16/446,121

(22) Filed: Jun. 19, 2019

(65) Prior Publication Data
US 2019/0304142 A1 Oct. 3, 2019

Related U.S. Application Data

(63) Continuation of application No. 15/721,689, filed on Sep. 29, 2017, now Pat. No. 10,339,677, which is a (Continued)

(51) Int. Cl.
*G01D 18/00* (2006.01)
*G21K 1/04* (2006.01)
(Continued)

(52) U.S. Cl.
CPC ............ *G06T 11/005* (2013.01); *A61B 6/032* (2013.01); *A61B 6/06* (2013.01); *A61B 6/5282* (2013.01);
(Continued)

(58) Field of Classification Search
CPC ......... A61B 6/032; A61B 6/06; A61B 6/5282; A61B 6/583; A61B 6/4035; A61B 6/08;
(Continued)

(56) References Cited

U.S. PATENT DOCUMENTS

| 4,787,098 A | 11/1988 | Silver |
| 5,331,552 A | 7/1994 | Lloyd et al. |

(Continued)

FOREIGN PATENT DOCUMENTS

| CN | 1438602 A | 8/2003 |
| CN | 104783822 A | 7/2015 |

OTHER PUBLICATIONS

International Search Report in PCT/CN2017/088569 dated Mar. 16, 2018, 4 pages.
(Continued)

*Primary Examiner* — Irakli Kiknadze
(74) *Attorney, Agent, or Firm* — Metis IP LLC

(57) ABSTRACT

The present disclosure relates to systems and methods for image data processing. A first correction coefficient corresponding to a first collimation width of a collimator of a scanner may be obtained. The collimator may have a collimation width being adjustable. A relationship between scattered radiation intensities and collimation widths may be obtained. A relationship between correction coefficients and collimation widths may be determined based on the first correction coefficient, the first collimation width, and the relationship between scattered radiation intensities and collimation widths. A target collimation width of the collimator may be obtained. A target correction coefficient may be determined based on the target collimation width and the relationship between correction coefficients and collimation widths.

20 Claims, 11 Drawing Sheets

Related U.S. Application Data continuation of application No. PCT/CN2017/088569, filed on Jun. 16, 2017.

(51) Int. Cl.
    *G06T 11/00*           (2006.01)
    *A61B 6/06*            (2006.01)
    *A61B 6/00*            (2006.01)
    *A61B 6/03*            (2006.01)
    *G01T 1/166*          (2006.01)
    *G01T 7/00*            (2006.01)

(52) U.S. Cl.
    CPC ............ *G01T 1/1663* (2013.01); *G01T 7/005* (2013.01); *A61B 6/583* (2013.01)

(58) Field of Classification Search
CPC ... A61B 6/4021; A61B 6/4085; A61B 6/4233; A61B 6/4258; A61B 6/482; A61B 6/5258; A61B 6/027; A61B 6/4042; A61B 6/4078; A61B 6/4266; A61B 6/4291; A61B 6/4441; A61B 6/4464; A61B 6/5205; G01T 1/1663; G01T 7/005; G01T 1/00; G01T 1/17; G01T 1/2985; G01T 1/1611; G01T 1/1644; G06T 11/005; A61N 5/1042; A61N 5/103; A61N 5/1045; A61N 2005/1087; A61N 2005/1095; A61N 5/1084; A61N 2005/1063; A61N 2005/1096; A61N 5/1043; A61N 5/1048; G21K 1/025; G21K 1/04; G21K 1/02; G02B 6/0096; G02B 6/0055; G02B 27/286; G02B 5/305; G02B 5/3083; G02B 6/0056; G02B 6/0076; G02B 6/0035; G02B 6/0036; G02B 6/0046; G02B 6/006; G02B 6/0063; G02B 6/0068; G01N 23/046; G01N 2223/419; G01N 2223/642; G01N 23/18; G01N 2223/612; G01N 23/083
USPC ........................ 378/70, 86–90, 147–155, 207
See application file for complete search history.

(56) References Cited

U.S. PATENT DOCUMENTS

| | | | |
|---|---|---|---|
| 9,155,508 | B2 | 10/2015 | Ueki |
| 9,226,720 | B2 * | 1/2016 | Tanaka ................. A61B 6/0457 |
| 10,339,677 | B2 * | 7/2019 | Yang |
| 2004/0213380 | A1 * | 10/2004 | Shaw ....................... A61B 6/06 378/145 |
| 2005/0025278 | A1 * | 2/2005 | Hagiwara ............... A61B 6/032 378/7 |
| 2007/0081622 | A1 | 4/2007 | Bruder et al. |
| 2011/0058644 | A1 | 3/2011 | Thran et al. |
| 2015/0173692 | A1 | 6/2015 | Heuscher |
| 2017/0135664 | A1 | 5/2017 | Takahashi et al. |

OTHER PUBLICATIONS

Written Opinion in PCT/CN2017/088569 dated Mar. 16, 2018, 4 pages.
First Office Action in Chinese Application No. 201710526757.8 dated Apr. 2. 2020, 14 pages.
First Office Action in Chinese Application No. 201710526857.0 dated Mar. 18, 2020, 16 pages.

* cited by examiner

SYSTEMS AND METHODS FOR IMAGE DATA PROCESSING IN COMPUTERIZED TOMOGRAPHY

CROSS-REFERENCE TO RELATED APPLICATIONS

This application is a continuation of U.S. patent application Ser. No. 15/721,689, filed on Sep. 29, 2017, which is a continuation of International Application No. PCT/CN2017/088569, filed on Jun. 16, 2017, the contents of each of which are hereby incorporated by reference.

TECHNICAL FIELD

The present disclosure generally relates to image data processing in computerized tomography (CT), and more particularly, to systems and methods for modifying image data related to a scanning based on a collimation width of the scanning.

BACKGROUND

A collimator is an importation component of a CT system. The collimator is positioned between an X-ray source and the scanned object (e.g. a patient) to control the scanning (e.g., a scanning region, a slice thickness). To improve imaging quality, image data collected in the CT system may be modified before image reconstruction. The modification of the image data may be associated with characteristics of the collimator, such as a collimation width. Thus, it may be desirable to develop systems and methods that modify image data based on the collimation width of the collimator.

SUMMARY

According to an aspect of the present disclosure, a system is provided. The system may include a scanner having a collimator, at least one processor, and at least one storage device storing a set of instructions. The collimator may have a collimation width being adjustable. The set of instructions, when executed by the at least one processor, cause the system to perform the following operations. The system may obtain a relationship between correction coefficients and collimation widths. The system may obtain a target collimation width of the collimator. The system may determine a target correction coefficient based on the target collimation width and the relationship between correction coefficients and collimation widths.

In some embodiments, the set of instructions, when executed by the at least one processor, cause the system to perform the following operations. The system may obtain image data related to a scanning with the target collimation width. The system may modify the image data based on the target correction coefficient.

In some embodiments, the set of instructions, when executed by the at least one processor, cause the system to perform the following operations. The system may obtain a first correction coefficient, the first correction coefficient corresponding to a first collimation width of the collimator. The system may obtain a relationship between scattered radiation intensities and collimation widths. The system may determine the relationship between correction coefficients and collimation widths based on the first correction coefficient, the first collimation width, and the relationship between scattered radiation intensities and collimation widths.

In some embodiments, when executed by the at least one processor, cause the system to save the determined relationship between correction coefficients and collimation widths to the one or more storage devices.

In some embodiments, when executed by the at least one processor, cause the system to perform the following operations. The system may instruct the scanner to scan a first object with the first collimation width. The system may obtain image data related to the first object based on the scanning of the first object. The system may process the image data related to the first object. The system may reconstruct an image of the first object based on the processed image data related to the first object. The system may determine the first correction coefficient corresponding to the first collimation width based on the reconstructed image of the first object.

In some embodiments, the first object may be a water phantom.

In some embodiments, when executed by the at least one processor, cause the system to instruct the scanner to scan air with the first collimation width.

In some embodiments, when executed by the at least one processor, cause the system to perform the following operations. The system may instruct the scanner to perform a first scanning of a second object with a second collimation width. The system may obtain a first radiation intensity based on the first scanning of the second object. The system may instruct the scanner to change the collimation width from the second collimation width to a third collimation width. The system may instruct the scanner to perform a second scanning of the second object with the third collimation width. The system may obtain a second radiation intensity based on the second scanning of the second object. The system may determine the relationship between radiation intensities and collimation widths based on the second collimation width, the first radiation intensity, the third collimation width, and the second radiation intensity. The system may determine the relationship between scattered radiation intensities and collimation widths based on the determined relationship between radiation intensities and collimation widths.

In some embodiments, the determination of the relationship between radiation intensities and collimation widths based on the second collimation width, the first radiation intensity, the third collimation width, and the second radiation intensity may be performed according to a curve fitting technique.

In some embodiments, when executed by the at least one processor, cause the system to determine a primary radiation intensity of the second object based on the relationship between radiation intensities and collimation widths.

In some embodiments, when executed by the at least one processor, cause the system to perform the following operations. The system may obtain a relationship between collimation widths and ratios of scattered radiation intensities over the primary radiation intensity of the second object. The system may designate the relationship between collimation widths and ratios of scattered radiation intensities over the primary radiation intensity of the second object as the relationship between scattered radiation intensities and collimation widths.

According to a further aspect of the present disclosure, a computer-implemented method for image data processing may include one or more of the following operations performed by at least one processor. At least one processor may obtain a relationship between correction coefficients and collimation widths. The at least one processor may obtain a target collimation width of the collimator of a scanner. The at least one processor may determine a target correction coefficient based on the target collimation width and the relationship between correction coefficients and collimation widths.

According to another aspect of the present disclosure, a non-transitory machine-readable storage medium may include instructions. When the non-transitory machine-readable storage medium accessed by at least one processor of a system, the instructions may cause the system to perform one or more of the following operations. The system may obtain a relationship between correction coefficients and collimation widths. The system may obtain a target collimation width of the collimator. The system may determine a target correction coefficient based on the target collimation width and the relationship between correction coefficients and collimation widths.

BRIEF DESCRIPTION OF THE DRAWINGS

The present disclosure is further described in terms of exemplary embodiments. These exemplary embodiments are described in detail with reference to the drawings. The drawings are not to scale. These embodiments are non-limiting exemplary embodiments, in which like reference numerals represent similar structures throughout the several views of the drawings, and wherein.

DETAILED DESCRIPTION

In the following detailed description, numerous specific details are set forth by way of examples in order to provide a thorough understanding of the relevant disclosure. However, it should be apparent to those skilled in the art that the present disclosure may be practiced without such details. In other instances, well known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

It will be understood that the term "system," "engine," "unit," "module," and/or "block" used herein are one method to distinguish different components, elements, parts, section or assembly of different level in ascending order. However, the terms may be displaced by other expression if they may achieve the same purpose.

Figure 2:
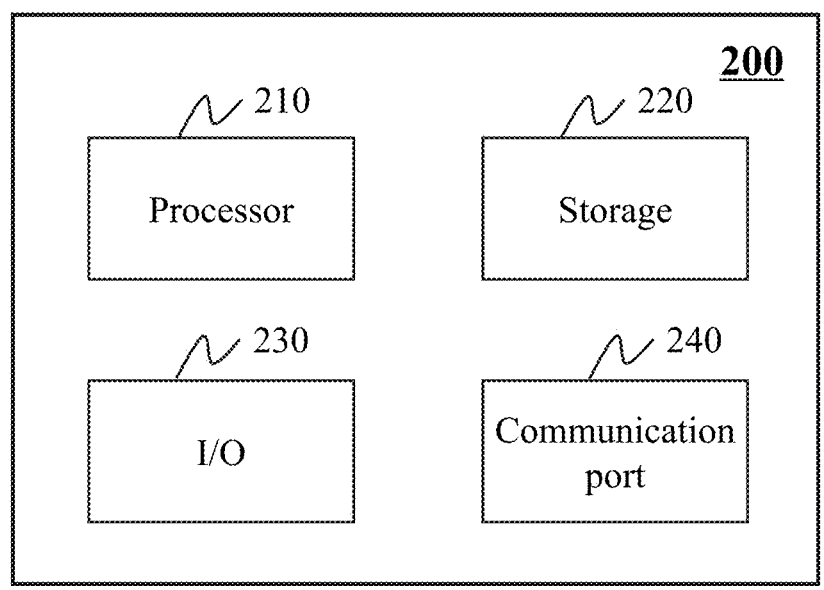
FIG. 2 is a schematic diagram illustrating hardware and/or software components of an exemplary computing device according to some embodiments of the present disclosure.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or other storage device. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices (e.g., processor 201 as illustrated in FIG. 2) may be provided on a computer readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in a firmware, such as an EPROM. It will be further appreciated that hardware modules/units/blocks may be included of connected logic components, such as gates and flip-flops, and/or can be included of programmable units, such as programmable gate arrays or processors. The modules/units/blocks or computing device functionality described herein may be implemented as software modules/units/blocks, but may be represented in hardware or firmware. In general, the modules/units/blocks described herein refer to logical modules/units/blocks that may be combined with other modules/units/blocks or divided into sub-modules/sub-units/sub-blocks despite their physical organization or storage.

It will be understood that when a unit, engine, module or block is referred to as being "on," "connected to," or "coupled to" another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

The terminology used herein is for the purposes of describing particular examples and embodiments only, and is not intended to be limiting. As used herein, the singular forms "a," "an," and "the" may be intended to include the plural forms as well, unless the context clearly indicates otherwise. It will be further understood that the terms "include" and/or "comprise," when used in this disclosure, specify the presence of integers, devices, behaviors, stated features, steps, elements, operations, and/or components, but do not exclude the presence or addition of one or more other integers, devices, behaviors, features, steps, elements, operations, components, and/or groups thereof.

Provided herein are systems and components for non-invasive imaging, such as for disease diagnosis or research purposes. In some embodiments, the imaging system may be a computed tomography (CT) system, an emission computed tomography (ECT) system, an X-ray photography system, a positron emission tomography (PET) system, or the like, or any combination thereof. For illustration purposes, the disclosure describes systems and methods for CT image data processing. The following description is provided to help better understand CT image data processing. The term "image" used in this disclosure may refer to a 2D image, a 3D image, or a 4D image. The term "image data" used in this disclosure may refer to CT data and projection data corresponding to the CT data. This is not intended to limit the scope the present disclosure. For persons having ordinary skills in the art, a certain amount of variations, changes, and/or modifications may be deducted under the guidance of the present disclosure. Those variations, changes, and/or modifications do not depart from the scope of the present disclosure.

An aspect of the present disclosure relates to systems and methods for modifying image data related to a scanning based on a collimation width of the scanning. A correction coefficient corresponding to the collimation width of the scanning may be determined to modify the image data. A first correction coefficient corresponding to a first collimation width may be determined by performing a scanning with the first collimation width. A target correction coefficient corresponding to a target collimation width may be determined based on the first collimation width, the first correction coefficient, and a relationship between radiation intensities and collimation widths. One of the purposes of the method is to determine the target correction coefficient corresponding to the target collimation width without performing a scanning with the target collimation width. As such, correction coefficients corresponding to the collimation widths in the CT system may be determined efficiently and quickly.

Figure 1:
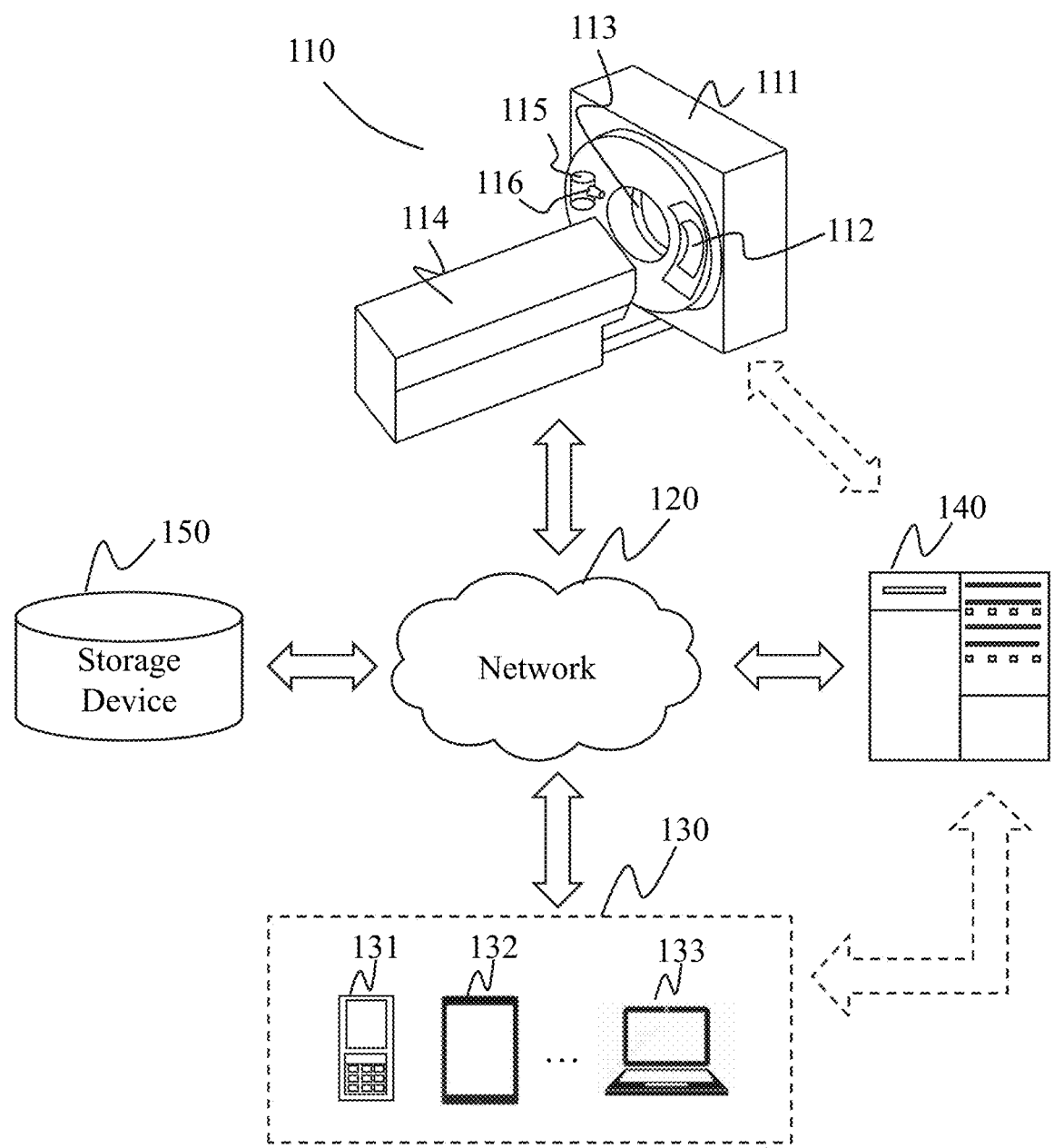
FIG. 1 is a schematic diagram illustrating an exemplary CT system according to some embodiments of the present disclosure.

FIG. 1 is a schematic diagram illustrating an exemplary CT system 100 according to some embodiments of the present disclosure. As shown, the CT system 100 may include a CT scanner 110, a network 120, one or more terminals 130, a processing device 140, and a database 150.

The CT scanner 110 may include a gantry 111, a detector 112, a detecting region 113, a table 114, a radioactive scanning source 115, and a collimator 116. The gantry 111 may be configured to support the detector 112 and the radioactive scanning source 115. A subject may be placed on the table 114 for scanning. The radioactive scanning source 115 may emit radioactive rays to the subject. The collimator 116 may be positioned between the radioactive scanning source 115 and the detector 112. The collimator 116 may control the scanning region of the radioactive rays generated by the radioactive scanning source 115. The detector 112 may detect radiation events (e.g., gamma photons) emitted from the detecting region 113. In some embodiments, the detector 112 may include one or more detector units. The detector units may include a scintillation detector (e.g., a cesium iodide detector), a gas detector, etc. The detector unit may include a single-row detector and/or a multi-rows detector.

The network 120 may include any suitable network that can facilitate exchange of information and/or data for the CT system 100. In some embodiments, one or more components of the CT system 100 (e.g., the CT scanner 110, the terminal 130, the processing device 140, the database 150, etc.) may communicate information and/or data with one or more other components of the CT system 100 via the network 120. For example, the processing device 140 may obtain image data from the CT scanner 110 via the network 120. As another example, the processing device 140 may obtain user instructions from the terminal 130 via the network 120. The network 120 may be and/or include a public network (e.g., the Internet), a private network (e.g., a local area network (LAN), a wide area network (WAN))), a wired network (e.g., an Ethernet network), a wireless network (e.g., an 802.11 network, a Wi-Fi network), a cellular network (e.g., a Long Term Evolution (LTE) network), a frame relay network, a virtual private network ("VPN"), a satellite network, a telephone network, routers, hubs, switches, server computers, and/or any combination thereof. Merely by way of example, the network 120 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or any combination thereof. In some embodiments, the network 120 may include one or more network access points. For example, the network 120 may include wired and/or wireless network access points such as base stations and/or internet exchange points through which one or more components of the CT system 100 may be connected to the network 120 to exchange data and/or information.

The terminal(s) 130 may include a mobile device 130-1, a tablet computer 130-2, a laptop computer 130-3, or the like, or any combination thereof. In some embodiments, the mobile device 130-1 may include a smart home device, a wearable device, a mobile device, a virtual reality device, an augmented reality device, or the like, or any combination thereof. In some embodiments, the smart home device may include a smart lighting device, a control device of an intelligent electrical apparatus, a smart monitoring device, a smart television, a smart video camera, an interphone, or the like, or any combination thereof. In some embodiments, the wearable device may include a bracelet, a footwear, eyeglasses, a helmet, a watch, clothing, a backpack, a smart accessory, or the like, or any combination thereof. In some embodiments, the mobile device may include a mobile phone, a personal digital assistance (PDA), a gaming device, a navigation device, a point of sale (POS) device, a laptop, a tablet computer, a desktop, or the like, or any combination thereof. In some embodiments, the virtual reality device and/or the augmented reality device may include a virtual reality helmet, virtual reality glasses, a virtual reality patch, an augmented reality helmet, augmented reality glasses, an augmented reality patch, or the like, or any combination thereof. For example, the virtual reality device and/or the augmented reality device may include a Google Glass™, an Oculus Rift™, a Hololens™, a Gear VR™, etc. In some embodiments, the terminal(s) 130 may be part of the processing device 140.

The processing device 140 may process data and/or information obtained from the CT scanner 110, the terminal 130, and/or the database 150.

In some embodiments, the processing device 140 may be a single server or a server group. The server group may be centralized or distributed. In some embodiments, the processing device 140 may be local or remote. For example, the processing device 140 may access information and/or data stored in the CT scanner 110, the terminal 130, and/or the database 150 via the network 120. As another example, the processing device 140 may be directly connected to the CT scanner 110, the terminal 130 and/or the database 150 to access stored information and/or data. In some embodiments, the processing device 140 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof. In some embodiments, the processing device 140 may be implemented by a computing device 200 having one or more components as illustrated in FIG. 2.

The database 150 may store data, instructions, and/or any other information. In some embodiments, the database 150 may store data obtained from the terminal 130 and/or the processing device 140. In some embodiments, the database 150 may store data and/or instructions that the processing device 140 may execute or use to perform exemplary methods described in the present disclosure. In some embodiments, the database 150 may include a mass storage, a removable storage, a volatile read-and-write memory, a read-only memory (ROM), or the like, or any combination thereof. Exemplary mass storage may include a magnetic disk, an optical disk, a solid-state drive, etc. Exemplary removable storage may include a flash drive, a floppy disk, an optical disk, a memory card, a zip disk, a magnetic tape, etc. Exemplary volatile read-and-write memory may include a random access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the database 150 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

In some embodiments, the database 150 may be connected to the network 120 to communicate with one or more other components of the CT system 100 (e.g., the processing device 140, the terminal 130). One or more components in the CT system 100 may access the data or instructions stored in the database 150 via the network 120. In some embodiments, the database 150 may be directly connected to or communicate with one or more other components of the CT system 100 (e.g., the processing device 140, the terminal 130). In some embodiments, the database 150 may be part of the processing device 140.

FIG. 2 is a schematic diagram illustrating exemplary hardware and/or software components of an exemplary computing device 200 on which the processing device 140 may be implemented according to some embodiments of the present disclosure. As illustrated in FIG. 2, the computing device 200 may include a processor 210, a storage 220, an input/output (I/O) 230, and a communication port 240.

The processor 210 may execute computer instructions (e.g., program code) and perform functions of the processing device 140 in accordance with techniques described herein. The computer instructions may include, for example, routines, programs, objects, components, data structures, procedures, modules, and functions, which perform particular functions described herein. For example, the processor 210 may process image data obtained from the CT scanner 110, the terminal 130, the database 150, and/or any other component of the CT system 100. In some embodiments, the processor 210 may include one or more hardware processors, such as a microcontroller, a microprocessor, a reduced instruction set computer (RISC), an application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an advanced RISC machine (ARM), a programmable logic device (PLD), any circuit or processor capable of executing one or more functions, or the like, or any combinations thereof.

Merely for illustration, only one processor is described in the computing device 200. However, it should be noted that the computing device 200 in the present disclosure may also include multiple processors, thus operations and/or method steps that are performed by one processor as described in the present disclosure may also be jointly or separately performed by the multiple processors. For example, if in the present disclosure the processor of the computing device 200 executes both operation A and operation B, it should be understood that operation A and operation B may also be performed by two or more different processors jointly or separately in the computing device 200 (e.g., a first processor executes operation A and a second processor executes operation B, or the first and second processors jointly execute operations A and B).

The storage 220 may store data/information obtained from the CT scanner 110, the terminal 130, the database 150, and/or any other component of the CT system 100. In some embodiments, the storage 220 may include a mass storage, a removable storage, a volatile read-and-write memory, a read-only memory (ROM), or the like, or any combination thereof. For example, the mass storage may include a magnetic disk, an optical disk, a solid-state drives, etc. The removable storage may include a flash drive, a floppy disk, an optical disk, a memory card, a zip disk, a magnetic tape, etc. The volatile read-and-write memory may include a random access memory (RAM). The RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. The ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage 220 may store one or more programs and/or instructions to perform exemplary methods described in the present disclosure. For example, the storage 220 may store a program for the processing device 140 for determining a regularization item.

The I/O 230 may input and/or output signals, data, information, etc. In some embodiments, the I/O 230 may enable a user interaction with the processing device 140. In some embodiments, the I/O 230 may include an input device and an output device. Examples of the input device may include a keyboard, a mouse, a touch screen, a microphone, or the like, or a combination thereof. Examples of the output device may include a display device, a loudspeaker, a printer, a projector, or the like, or a combination thereof. Examples of the display device may include a liquid crystal display (LCD), a light-emitting diode (LED)-based display, a flat panel display, a curved screen, a television device, a cathode ray tube (CRT), a touch screen, or the like, or a combination thereof.

The communication port 240 may be connected to a network (e.g., the network 120) to facilitate data communications. The communication port 240 may establish connections between the processing device 140 and the CT scanner 110, the terminal 130, and/or the database 150. The connection may be a wired connection, a wireless connection, any other communication connection that can enable data transmission and/or reception, and/or any combination of these connections. The wired connection may include, for example, an electrical cable, an optical cable, a telephone wire, or the like, or any combination thereof. The wireless connection may include, for example, a Bluetooth™ link, a Wi-Fi™ link, a WiMax™ link, a WLAN link, a ZigBee link, a mobile network link (e.g., 3G, 4G, 5G, etc.), or the like, or a combination thereof. In some embodiments, the communication port 240 may be and/or include a standardized communication port, such as RS232, RS485, etc. In some embodiments, the communication port 240 may be a specially designed communication port. For example, the communication port 240 may be designed in accordance with the digital imaging and communications in medicine (DICOM) protocol.

Figure 3:
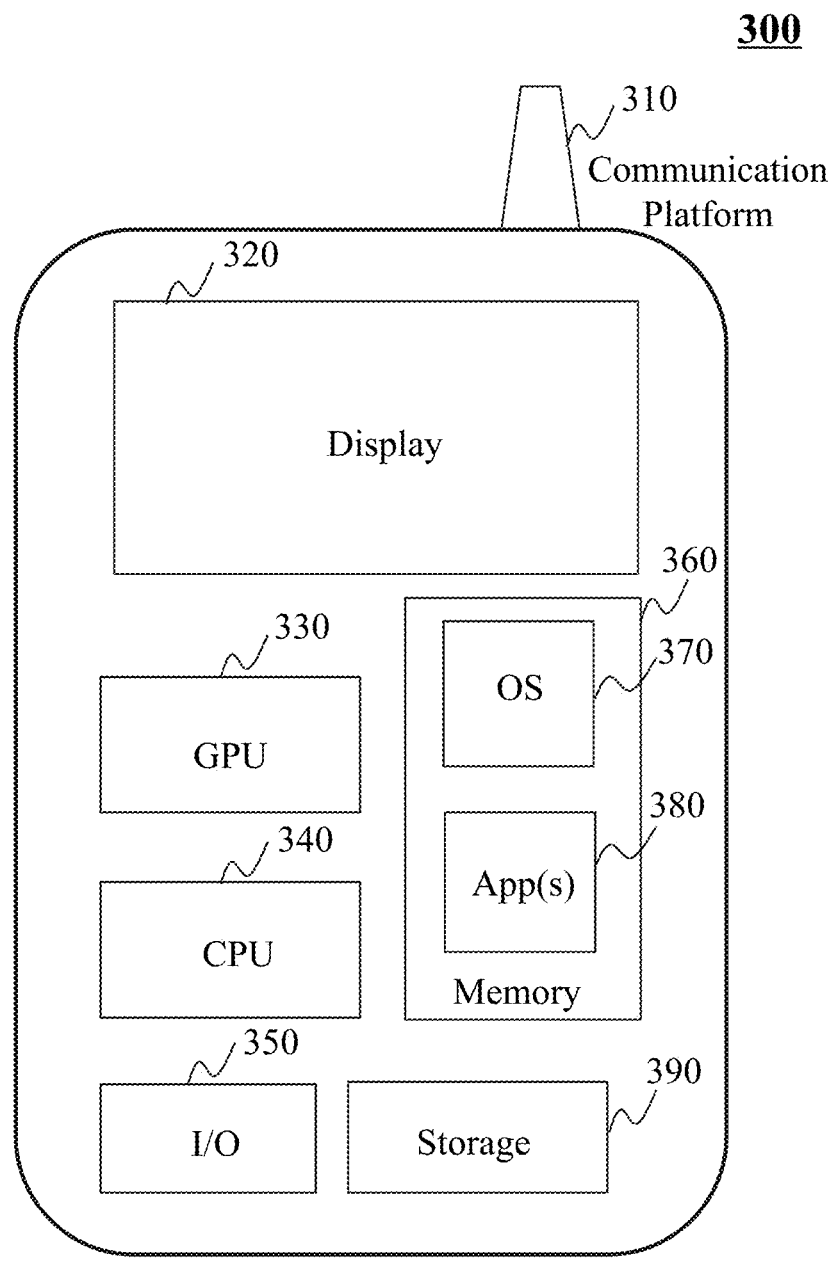
FIG. 3 is a schematic diagram illustrating hardware and/or software components of an exemplary mobile device according to some embodiments of the present disclosure.

FIG. 3 is a schematic diagram illustrating exemplary hardware and/or software components of an exemplary mobile device 300 on which the terminal 130 may be implemented according to some embodiments of the present disclosure. As illustrated in FIG. 3, the mobile device 300 may include a communication platform 310, a display 320, a graphic processing unit (GPU) 330, a central processing unit (CPU) 340, an I/O 350, a memory 360, and a storage 390. In some embodiments, any other suitable component, including but not limited to a system bus or a controller (not shown), may also be included in the mobile device 300. In some embodiments, a mobile operating system 370 (e.g., iOS™, Android™, Windows Phone™) and one or more applications 380 may be loaded into the memory 360 from the storage 390 in order to be executed by the CPU 340. The applications 380 may include a browser or any other suitable mobile apps for receiving and rendering information relating to image processing or other information from the processing device 140. User interactions with the information stream may be achieved via the I/O 350 and provided to the processing device 140 and/or other components of the CT system 100 via the network 120.

To implement various modules, units, and their functionalities described in the present disclosure, computer hardware platforms may be used as the hardware platform(s) for one or more of the elements described herein. A computer with user interface elements may be used to implement a personal computer (PC) or any other type of work station or terminal device. A computer may also act as a server if appropriately programmed.

Figure 4A:
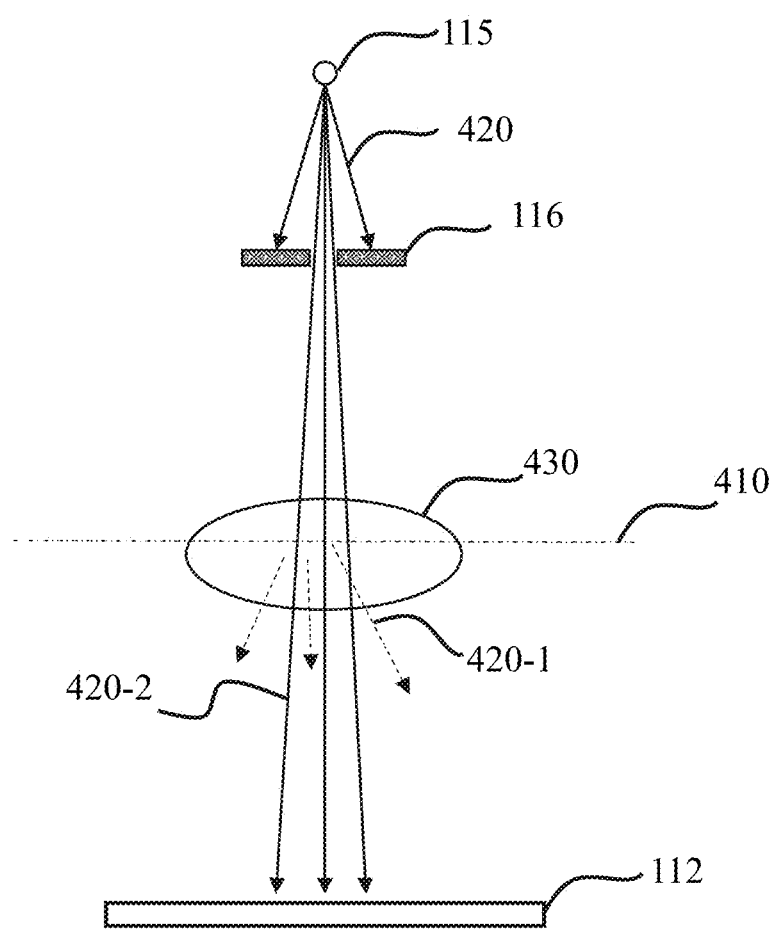
FIG. 4A is schematic diagram illustrating an exemplary scanning according to some embodiments of the present disclosure.

FIG. 4A is schematic diagram illustrating an exemplary scanning according to some embodiments of the present disclosure. As shown in FIG. 4A, the radioactive scanning source 115 may emit radioactive rays 420 to an object 430.

In some embodiments, the radioactive rays 420 may be X-rays. The object 430 may be an experimental object, an organ, tissue, or any body parts of a patient to be scanned. The collimator 116 may be positioned between the radioactive scanning source 115 and the object 430.

In some embodiments, the collimator 116 may include two collimator plates that are separated from each other. The collimator plates may be made of X-ray absorbing material, such as lead or tungsten. The radioactive rays irradiated on the collimator plates may be absorbed, and the rest may reach the object 430. The collimator 116 may include a space between the two collimator plates. The number of radiation rays irradiated on the object 430 may depend with the size of the space. For example, the number of radiation rays irradiated on the object 430 may increase with the increase in a distance between the two collimator plates.

The radiation rays passing through the space between the two collimator plates may pass through an isocenter surface 410. The isocenter surface 410 refers to a surface that passes the rotation isocenter of the gantry 110. In some embodiments, the isocenter surface 410 may be parallel with the collimator plates. The radiation rays passing through the space 440 may have an irradiation region on the isocenter surface 410. A collimation width of the collimator 116 refers to the largest distance between two points in the irradiation region among any two points in the irradiation region. The collimation width of the collimator 116 may depend with the distance between the two collimator plates. For example, the collimation width may increase with the increase in the distance between the two collimator plates.

The collimation width may be set manually by a user (e.g., a technician, a doctor, a nurse) via the terminal 130 or the processing device 140. Additionally or alternatively, the collimation width may be determined by one or more components of the CT system 100. In some embodiments, the processing device 140 may determine a collimation width based on the distance between the two collimator plates, a distance between the radioactive scanning source 115 and the collimator 116, and a distance between the radioactive scanning source 115 and the isocenter surface 410. Merely by way of example, the processing device 140 may divide the distance between the radioactive scanning source 115 and the isocenter surface 410 by the distance between the radioactive scanning source 115 and the collimator 116 to obtain a quotient. The processing device 140 may then determine the collimation width by multiplying the distance between the two collimator plates by the quotient. In some embodiments, the distance between the radioactive scanning source 115 and the collimator 116 may be in a range of 180-210 mm (e.g., 190 mm). The distance between the radioactive scanning source 115 and the isocenter surface 410 may be in a range of 500-600 mm (e.g., 570 mm).

The radioactive rays irradiated on the object 430 may pass through the object 430, be absorbed by the object 430, or be scattered by the object 430. The radioactive rays passing through the object 430 (e.g., a radioactive ray 420-2) are referred to herein as a primary radiation. The radiation rays scattered by the object 430 (e.g., a radioactive ray 420-1) are referred to herein as a scattered radiation. Different scanned objects or different parts of a scanned object may have a same absorption rate or different absorption rates of radioactive rays. Different scanned objects or different parts of the scanned object may have a same scattering rate or different scattering rates of radioactive rays.

The radiations, including the primary radiation and the scattered radiation, may be detected by the detector 112. In some embodiments, the processing device 140 may determine the radiation intensity of the primary radiation and the scattered radiation based on the radiations received by the detector 112. The radiation intensity may be equal to a sum of a primary radiation intensity and a scattered radiation intensity. When the collimation width of the collimator 116 changes, the scattered radiation intensity may change, but the primary radiation intensity may remain constant. For example, the scattered intensity may increase with the increase in the collimation width. Accordingly, the radiation intensity may increase with the increase in the collimation width.

It should be noted that the above descriptions are provided for the purposes of illustration, and not intended to limit the scope of the present disclosure. For persons having ordinary skills in the art, various modifications and changes in the forms and details of the application of the above method and system may occur without departing from the principles of the present disclosure. For example, the collimator 116 may be arranged in any position between the radioactive scanning source 115 and the object 430. As another example, the collimator 116 may have any shape, size, and configuration. In some embodiments, the collimator 116 may be an integral plate with a hole. A portion of the radioactive rays 420 may pass through the hole to irradiate the object 430. The amount of radioactive rays irradiated on the object 430 may be related to the size of the hole. However, those variations and modifications also fall within the scope of the present disclosure.

Figure 4B:
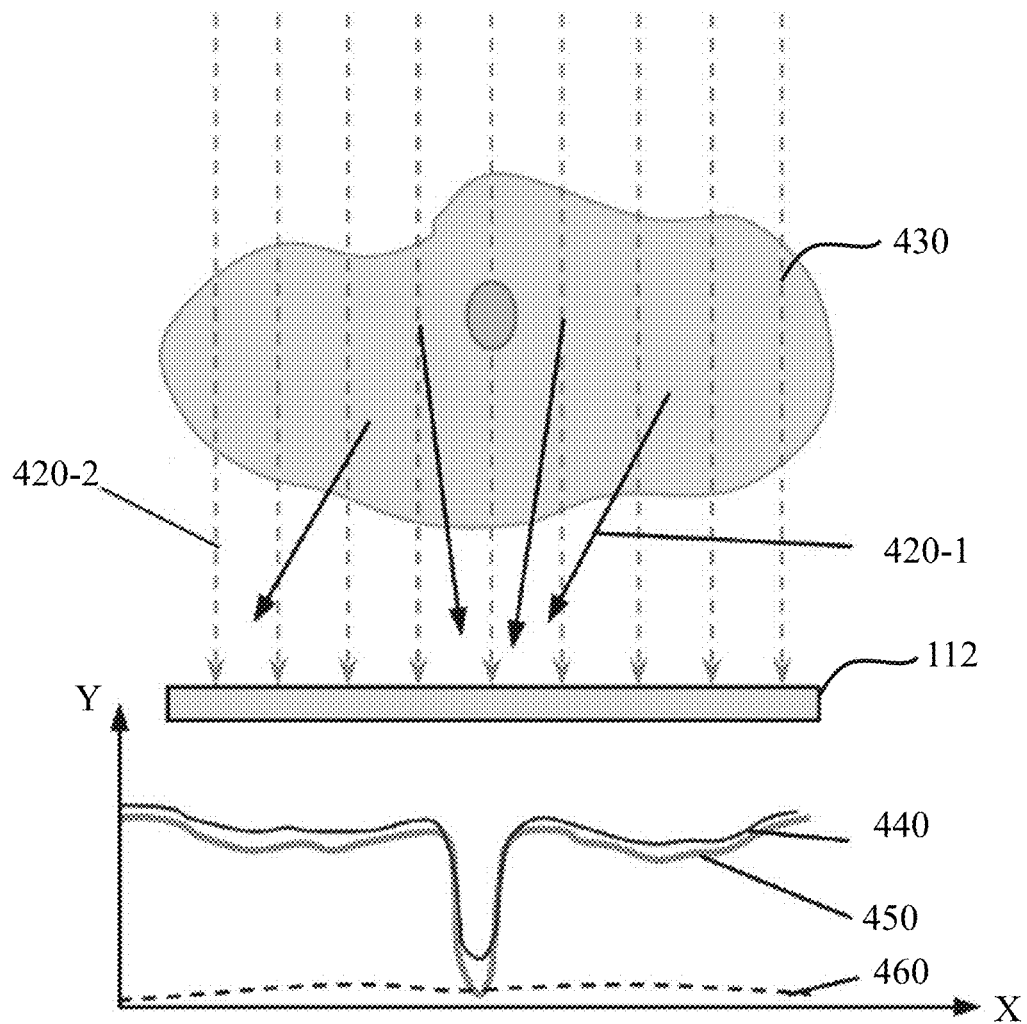
FIG. 4B is schematic diagram illustrating an exemplary radiation intensity distribution according to some embodiments of the present disclosure.

FIG. 4B is schematic diagram illustrating an exemplary radiation intensity distribution according to some embodiments of the present disclosure. The X-axis corresponds to different parts of the object 430 in the horizontal direction. The Y-axis corresponds to the radiation intensity. Curve 440 indicates a distribution of a total radiation intensity related to the object 430, including the radiation intensity of the primary radiation and the radiation intensity of the scattered radiation. Curve 450 indicates a distribution of the radiation intensity of the primary radiation. Curve 460 indicates a distribution of the radiation intensity of the scattered radiation. The total radiation intensity may be determined by the processing device 140 based on radiations received by the detector 112. The total radiation intensity of the object 430 is equal to a sum of a scattered radiation intensity and a primary radiation intensity.

It should be noted that the examples of radiation intensity distributions illustrated in FIG. 4B are provided for the purposes of illustration, and not intended to limit the scope of the present disclosure. For persons having ordinary skills in the art, various modifications and changes in the forms and details of the application of the above method and system may occur without departing from the principles of the present disclosure. For example, the total radiation intensity, the scattered radiation intensity, and the primary radiation intensity may have any distribution pattern, respectively.

Figure 5:
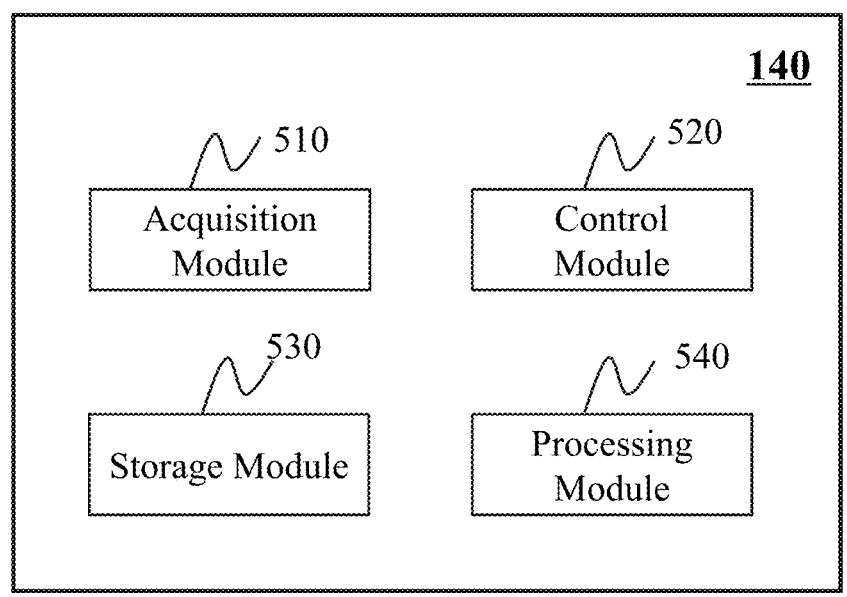
FIG. 5 is a block diagram illustrating an exemplary processing engine according to some embodiments of the present disclosure.

FIG. 5 is a block diagram illustrating an exemplary processing device 140 according to some embodiments of the present disclosure. The processing device 140 may include an acquisition module 510, a control module 520, a storage module 530, and a processing module 540.

The acquisition module 510 may acquire image data. The acquisition module 510 may acquire the image data from the detector 112. The image data may include CT data, projection data corresponding to the CT data, an image (e.g., a 2D image, a 3D image, a 4D image data). The image data may include information related to the radiations that pass through and/or be scattered by an object. In some embodiments, the radioactive scanning source 115 may emit the radiations toward the object. The radiations may pass through the object or be scattered by the object and may attenuate during the transmission process. The attenuated radiations may be detected by the detector 112 and reflected in the image data transmitted to the acquisition module 510. In some embodiments, the acquired image data may be transmitted to the storage module 530 for storage.

The control module 520 may control operations of one or more components in the CT system 100, such as the acquisition module 510, the storage module 530, the processing module 540, and/or the CT scanner 110 (e.g., by generating one or more control signals or parameters). For example, the control module 520 may control the acquisition module 510 to acquire a signal, the timing of the acquisition of the signal, etc. As another example, the control module 520 may control the processing module 540 to process the image data acquired by the acquisition module 510. In some embodiments, the control module 520 may receive a real-time command or retrieve a predetermined command provided by a user (e.g., a doctor) to control one or more operations of the acquisition module 510 and/or the processing module 540. In some embodiments, the control module 520 may communicate with one or more other modules of the processing device 140 for exchanging information and/or data. In some embodiments, the control module 520 may set one or more scanning parameters. The scanning parameters may include a distance between the radioactive scanning source 115 and the collimator 116, a distance between the radioactive scanning source 115 and a scanned object, a distance between the collimator 116 and the detector 112, a collimation width of the collimator 116, a radiation dosage, or the like, or any combination thereof.

The storage module 530 may store image data, control parameters, processed data generated by various modules of the processing device 140, or the like, or a combination thereof. In some embodiments, the storage 530 may store one or more programs and/or instructions that may be executed by the processor(s) of the processing device 140 to perform exemplary methods described in this disclosure. For example, the storage 530 may store program(s) and/or instruction(s) that can be executed by the processor(s) of the processing device 140 to perform the functions thereof disclosed in this disclosure (e.g., acquiring image data, processing the image data, reconstructing an image based on the image data or the processed image data). As another example, storage module 530 may store a relationship between collimation widths and scattered radiation intensities, a relationship between collimation widths and correction coefficients, and/or a relationship between collimation widths and ratios of scattered radiation intensities over the primary radiation intensity.

The processing module 540 may process information provided by various modules of the processing device 140. The processing module 540 may process image data acquired by the acquisition module 510, image data retrieved from the storage module 530, etc. For example, the processing module 540 may determine a correction coefficient corresponding to a collimation width of a scanning. Additionally or alternatively, the processing module 540 may modify image data associated with the scanning based on the correction coefficient.

In some embodiments, the processing module 540 may reconstruct CT images based on the image data according to a reconstruction algorithm, generate reports including one or more CT images and/or other related information, and/or perform any other function for image reconstruction in accordance with various embodiments of the present disclosure. The reconstruction algorithm may include an iterative reconstruction algorithm (e.g., a statistical reconstruction algorithm), a Fourier slice theorem algorithm, a filtered back projection (FBP) algorithm, a fan-beam reconstruction algorithm, an analytic reconstruction algorithm, or the like, or any combination thereof.

In some embodiments, one or more modules illustrated in FIG. 5 may be implemented in at least part of the exemplary CT system as illustrated in FIG. 1. For example, the acquisition module 510, the control module 520, the storage module 530, and/or the processing module 540 may be integrated into a console (not shown). Via the console, a user may set parameters for scanning an object (e.g., a collimation width of the collimator), controlling imaging processes, controlling parameters for reconstruction of an image, viewing reconstructed images, etc. In some embodiments, the console may be implemented via the processing device 140 and/or the terminal 130.

Figure 6:
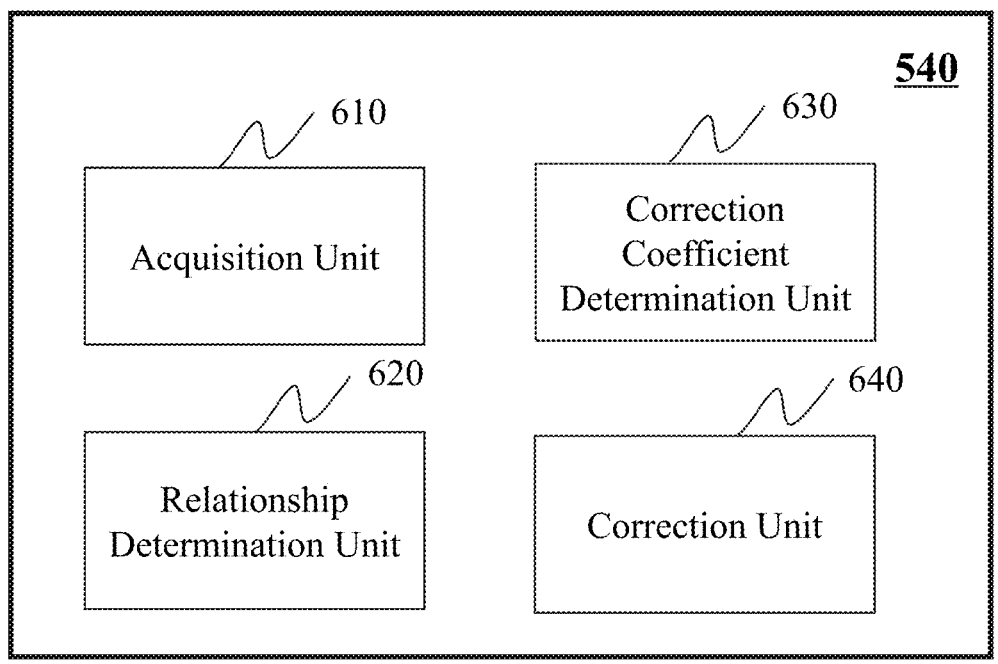
FIG. 6 is a block diagram illustrating an exemplary processing module according to some embodiments of the present disclosure.

FIG. 6 is a block diagram illustrating an exemplary processing module 540 according to some embodiments of the present disclosure. The processing module 540 may include an acquisition unit 610, a relationship determination unit 620, a correction coefficient determination unit 630, and a correction unit 640. The processing module 540 may be implemented on various components (e.g., the processor 210 of the computing device 200 as illustrated in FIG. 2).

The acquisition unit 610 may obtain image data related to a scanning. The image data may be obtained from other component in the CT system 100, such as the storage device 150 or the storage module 430. The image data may be associated with the radiations that pass through and/or be scattered by a scanned object in the scanning.

The relationship determination unit 620 may obtain and/or determine one or more relationships between parameters related to the CT system 100. The one or more relationships may include but are not limited to a relationship between collimation widths and scattered radiation intensities, a relationship between correction coefficients and collimation widths, and/or a relationship between collimation widths and ratios of scattered radiation intensities over the primary radiation intensity. In some embodiments, the relationship determination unit 620 may obtain at least part of the one or more relationships from a storage device (e.g., the storage device 150, the storage 220). In some embodiments, the relationship determination unit 620 may determine at least part of the one or more relationships based on data analyzing.

The correction coefficient determination unit 630 may determine a correction coefficient corresponding to a collimation width of a scanning. In some embodiments, the correction coefficient determination unit 630 may determine the correction coefficient corresponding to the collimation width based a scanning of an object with the collimation width. For example, the correction coefficient determination unit 630 may determine the correction coefficient corresponding to the collimation width based on a reconstructed image generated based on the scanning with the collimation width. In some embodiments, the correction coefficient determination unit 630 may determine the correction coefficient corresponding to the collimation width based on a relationship between collimation widths and correction coefficients. The relationship may be stored in a storage device (e.g., the storage device 150, the storage 220). The relationship may be recorded in the form of a table, a drawing, a mathematical expression, etc. The correction coefficient determination unit 630 may retrieve the relationship from the storage device and determine the correction coefficient corresponding to the collimation width based on the relationship.

The correction unit 640 may the correction unit 640 may modify image data based on a correction coefficient. In some embodiments, the correction unit 640 may modify the image data by multiplying the image data with the correction coefficient. For example, the image data may include projection data related to the scanning. For illustration purpose, assuming that the correction coefficient is equal to eight, the correction unit 640 may obtain modified projection data that is equal to eight times of the projection data.

It should be noted that the above descriptions of the processing device 140 and/or the processing module 540 are provided for the purposes of illustration, and not intended to limit the scope of the present disclosure. For persons having ordinary skills in the art, various modifications and changes in the forms and details of the application of the above method and system may occur without departing from the principles of the present disclosure. In some embodiments, the processing module 540 may include one or more other modules. For example, the processing module 540 may include a storage module to store data generated by the modules in the processing module 540. As another example, the relationship determination unit 620 may include a radiation intensity determination subunit to determine a radiation intensity related to a scanning based on image data of a scanning. In some embodiments, one module may perform the functions of two or more modules described above. For example, the correction coefficient determination unit 630 and the correction unit 640 may form a module to determine the correction coefficient and correction image data based on the determined correction coefficient. However, those variations and modifications also fall within the scope of the present disclosure.

Figure 7:
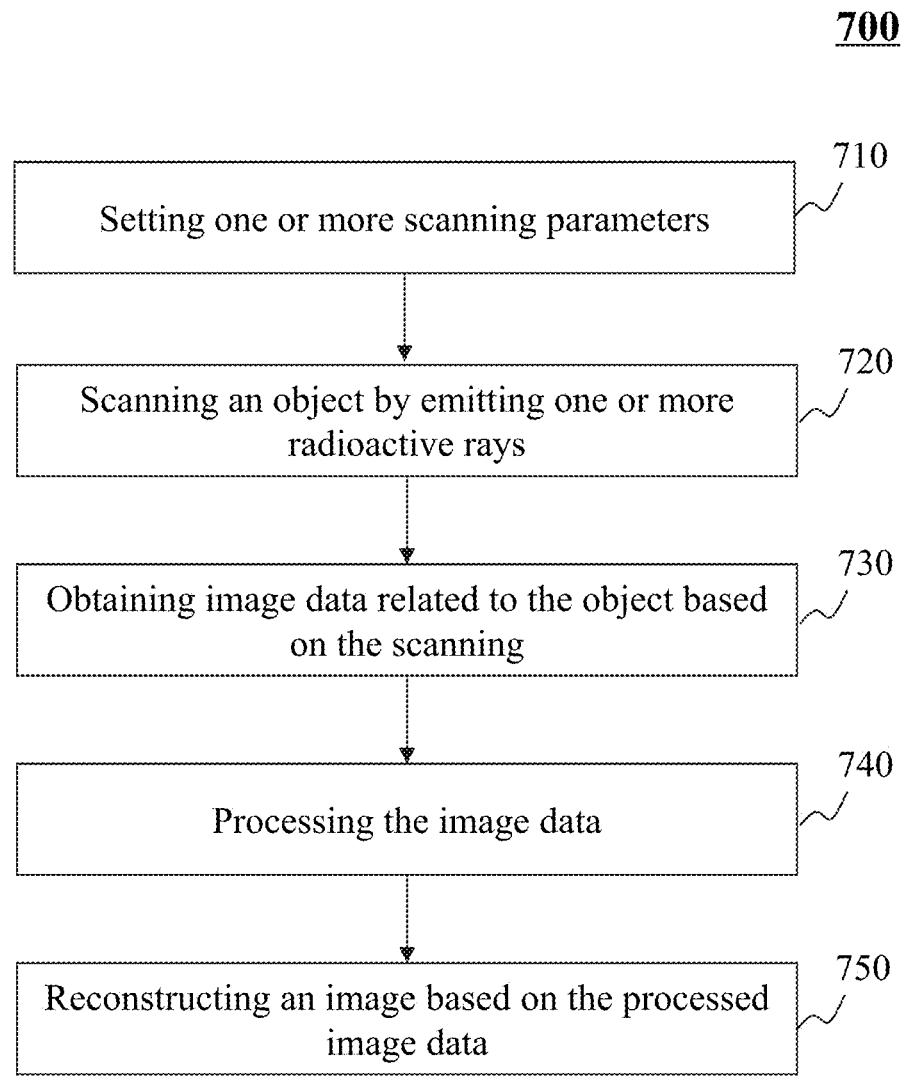
FIG. 7 is a flowchart illustrating an exemplary process for image generation in computerized tomography according to some embodiments of the present disclosure.

FIG. 7 is a flowchart illustrating an exemplary process for image generation in computerized tomography according to some embodiments of the present disclosure. In some embodiments, at least part of the process 700 may be performed by the processing device 140 (implemented in, for example, the computing device 200 shown in FIG. 2).

In 710, the control module 520 may set one or more scanning parameters. The scanning parameters may include a distance between the radioactive scanning source 115 and the collimator 116, a distance between the radioactive scanning source 115 and a scanned object, a distance between the collimator 116 and the detector 112, a collimation width of the collimator 116, a radiation dosage, or the like, or any combination thereof. In some embodiments, the scanning parameters may be default parameters stored in a storage device (e.g., the storage device 150) or set by a user (e.g., a doctor) of the CT system 100. Alternatively or additionally, the scanning parameters may be determined by one or more components (e.g., the processing device 140) in the CT system 100. In some embodiments, in 710, the control module 520 may set the collimation width of the collimator 116. The collimation width may be 2 mm, 5 mm, 10 mm, 20 mm, 40 mm or any other suitable width.

In 720, the radioactive scanning source 115 may scan an object by emitting one or more radioactive rays. In some embodiments, the radioactive rays may be X-rays. The object may be an experimental object, an organ, tissue, or any body parts of a patient to be scanned. In some embodiments, some of the radioactive rays may pass through the space between the collimator plates (having a width W), and the rest may be absorbed by the collimator plates. The radioactive rays that pass through the space between the collimator plates may be irradiated on the object. The radioactive rays irradiated on the object may pass through the object or be scattered by the object. The radioactive rays passing through the object may be referred herein as primary radiations and the radiation rays scattered by the object may be referred herein as scattered radiations as described elsewhere in this disclosure (e.g., FIG. 4A and the relevant descriptions).

In 730, the acquisition module 510 may obtain image data related to the object based on the scanning. The image data may be associated with the radiations that pass through and/or be scattered by the object. The radiations, which may include the primary radiations and the scattered radiations, may attenuate during transmission process. The attenuated radiations may be detected by the detector 112, and the image data related to the attenuated radiations may be obtained by the acquisition module 510.

In 740, the processing device 140 (e.g., the processing module 540) may process the image data. The image data processing may include one or more data processing operations, such as data projection, data filtering, data sequencing, data modifying, curve fitting. In some embodiments, the image data may be modified based on a correction coefficient of a Hounsfield unit (HU) value of a voxel (as referred herein as the correction coefficient). The correction coefficient may indicate a relative ratio of an attenuation coefficient of the voxel to an attenuation coefficient of water. The HU value of the voxel may be described according to Equation (1) below:

$$HU = \frac{\mu - \mu_{water}}{\mu_{water}} * 1000 = \mu * \frac{1000}{\mu_{water}} - 1000,  \quad \text{Equation (1)}$$

where $\mu$ refers to the attenuation coefficient of the voxel, and $\mu_{water}$ refers to the attenuation coefficient of water.

The correction coefficient may be determined based on Equation (1) and described according to Equation (2) below:

$$C = \frac{1000}{\mu_{water}},  \quad \text{Equation (2)}$$

where C refers to the correction coefficient of the HU value of the voxel.

The correction coefficient may be associated with one or more scanning parameters described in connection with step 710. In some embodiments, the correction coefficient may be associated with the collimation width of the collimator 116. For example, the correction coefficients corresponding to different collimation widths may be different.

In some embodiments, the processing device 140 (e.g., the correction coefficient determination unit 630) may determine a correction coefficient corresponding to the collimation width of the scanning. The processing device 140 (e.g., the correction unit 640) may also modify the image data based on the correction coefficient. For example, the processing device 140 may determine the correction coefficient corresponding to the collimation width based on a relationship between collimation widths and correction coefficients. The relationship between collimation widths and correction coefficients may be stored in a storage device (e.g., the storage device 150, the storage 220), and the processing device 140 may retrieve the relationship from the storage device. Alternatively or additionally, the relationship between collimation widths and correction coefficients may be determined by the processing device 140 based on experimental data. More descriptions regarding the modifying image data based on the correction coefficient corresponding to the collimation width may be found elsewhere in the present disclosure (e.g., FIG. 8 and the relevant descriptions).

In 750, the processing module 540 may reconstruct an image based on the processed (or modified) image data. The reconstructed image may include a 3D image, 4D image data, a 4D image, or the like, or any combination thereof. The processing module 540 may reconstruct the image based on the processed (or modified) image data according to a reconstruction algorithm. The reconstruction algorithm may include an iterative reconstruction algorithm (e.g., a statistical reconstruction algorithm), a Fourier slice theorem algorithm, a filtered back projection (FBP) algorithm, a fan-beam reconstruction algorithm, an analytic reconstruction algorithm, or the like, or any combination thereof.

Figure 8:
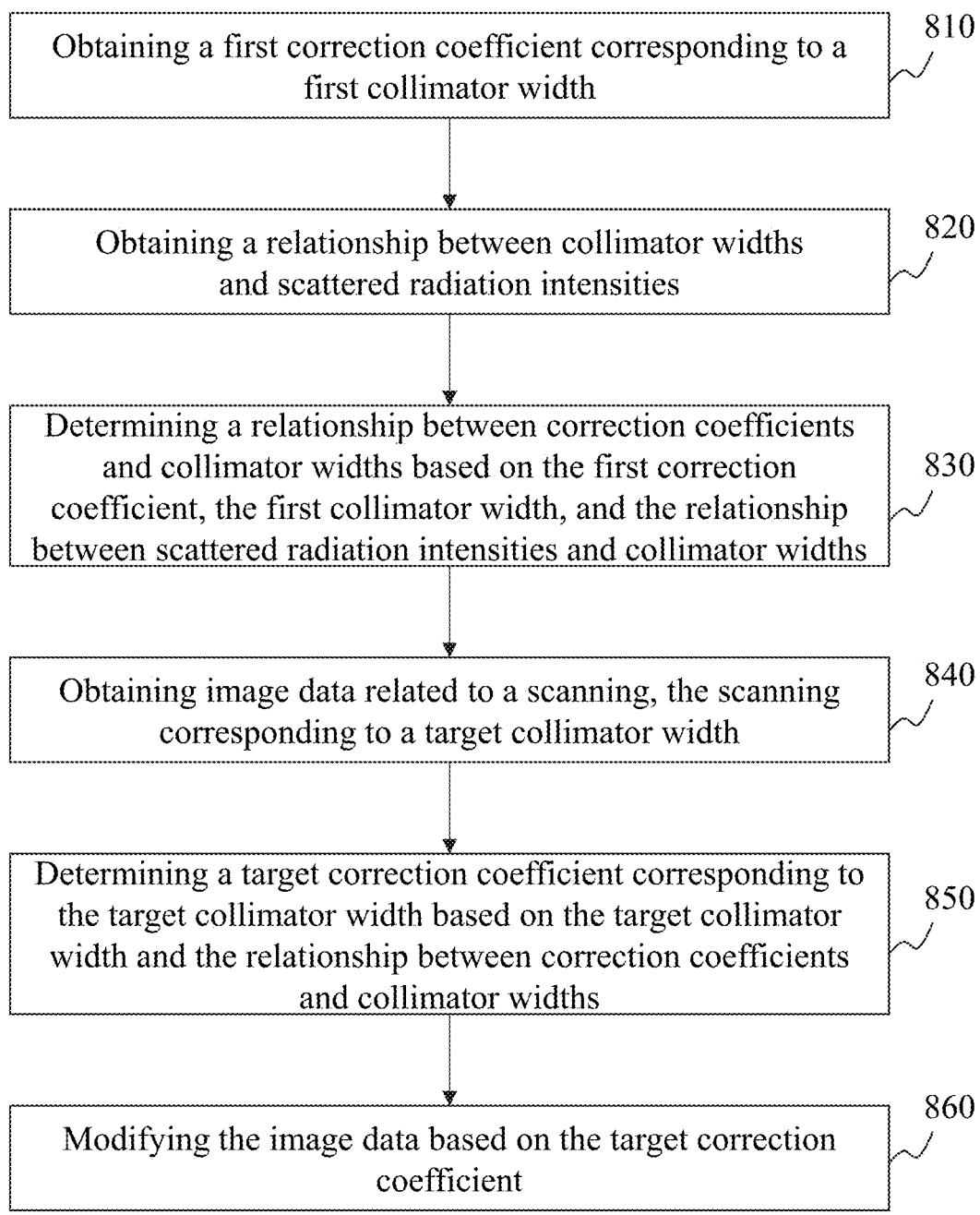
FIG. 8 is a flowchart illustrating an exemplary process for processing image data in computerized tomography according to some embodiments of the present disclosure.

It should be noted that the above descriptions of process 700 are provided for the purposes of illustration, and not intended to limit the scope of the present disclosure. For persons having ordinary skills in the art, various modifications and changes in the forms and details of the application of the above method and system may occur without departing from the principles of the present disclosure. In some embodiments, one or more operations may be added or omitted. For example, step 750 may be omitted. As another example, an additional operation may be performed to display the reconstructed image on the terminal 130. However, those variations and FIG. 8 is a flowchart illustrating an exemplary process for processing image data in computerized tomography according to some embodiments of the present disclosure. In some embodiments, at least part of the process 800 may be performed by the processing device 140 (implemented in, for example, the computing device 200 shown in FIG. 2).

In 810, the correction coefficient determination unit 630 may obtain a first correction coefficient corresponding to a first collimation width. The CT scanner 110 may scan an object with the first collimation width, and the correction coefficient determination unit 630 may determine the first correction coefficient corresponding to the first collimation width based on the scanning of the object. More descriptions regarding the determination of the first correction coefficient corresponding to the first collimation width may be found elsewhere in the present disclosure (e.g., FIG. 9 and the relevant descriptions)

In 820, the relationship determination unit 620 may obtain a relationship between collimation widths and scattered radiation intensities. The relationship may be recorded in the form of a table, a drawing, a mathematical expression, etc. For example, the relationship may be recorded in a table of collimation widths and their corresponding scattered radiation intensities (e.g., a look-up table) stored in a storage device (e.g., the storage device 150, the storage 220). The relationship determination unit 620 may access the storage device and retrieve the relationship. As another example, the relationship may be recorded in a mathematical function. The mathematical function may include at least two variables: the scattered radiation intensity and the collimation width. Alternatively, the mathematical function may include other variables that may affect the relationship between collimation widths and scattered radiation intensities, such as one or more scanning parameters as described in connection with FIG. 7. The mathematical function may be a linear function, an inverse function, a quadratic function, a discontinuous function, a trigonometric functions, an injective function, a surjective function, or the like, or any combination thereof. In some embodiments, the mathematical function may be a linear function with the collimation width being an independent variable and the scattered radiation intensity being a dependent variable.

In some embodiments, the relationship determination unit 620 may obtain the relationship between collimation widths and scattered radiation intensities from other component in the CT system 100, such as the storage device 150 or the storage module 430. In some embodiments, the relationship determination unit 620 may determine the relationship between collimation widths and scattered radiation intensities based on experiment data. For example, the CT scanner 110 may perform an experiment by scanning an experimental object with different collimation widths. The processing device 140 may determine radiation intensities corresponding to the different collimation widths based on image data collected by the detector 112. As another example, the processing device 140 may simulate an experiment of scanning an experimental object with different collimation widths and determine radiation intensities corresponding to the different collimation widths. The relationship determination unit 620 may obtain the experimental data related to the performed experiment or the simulated experiment and determine the relationship between collimation widths and scattered radiation intensities based on the experimental data. The determination of the relationship between collimation widths and scattered radiation intensities may include one or more data processing operations of the experimental data. Exemplary data processing operations may include but are not limited to data sequencing, data filtering, curve fitting.

In some embodiments, the relationship between collimation widths and scattered radiation intensities may be determined based on a relationship between radiation intensities and collimation widths. More descriptions regarding the determination of the relationship between collimation widths and scattered radiation intensities of may be found elsewhere in the present disclosure (e.g., FIG. 10 and the relevant descriptions)

In 830, the relationship determination unit 620 may determine a relationship between correction coefficients and collimation widths based on the first correction coefficient, the first collimation width, and the relationship between collimation widths and scattered radiation intensities. For illustration purpose, the relationship between collimation widths and scattered radiation intensities may be described according to Equation (3) below:

$$S = f(w) \qquad \text{Equation (3)},$$

where S refers to the scattered radiation intensity, w refers to the collimation width.

The correction coefficient of the image data may be determined based on the u value of water according to Equation (2) as described elsewhere in this disclosure (e.g., FIG. 7 and the relevant descriptions). The u value of water may be proportional to a radiation intensity (i.e., a sum of a scattered radiation intensity and a primary radiation intensity) received by the detector 112. The primary radiation intensity may have a constant value. More descriptions regarding the determination of primary radiation intensity may be found elsewhere in the present disclosure (e.g., FIG. 10 and the relevant descriptions). The relationship between collimation widths and radiation intensities may be described according to Equation (4) below:

$$\frac{1000}{C_w} = c * (f(w) + P), \qquad \text{Equation (4)}$$

where $C_w$ refers to the correction coefficient corresponding to the collimation width w, P refers to the primary radiation intensity, c refers to a coefficient that may be determined according to Equation (5) below $$C = \frac{1000}{C_{w1} * (f(w1) + P)}, \qquad \text{Equation (5)}$$

where w1 refers to the first collimation width, $C_{w1}$ refers to the first correction coefficient corresponding to the first collimation width w1 (as described in connection with operation 810), f(w1) refers to the scattered radiation intensity corresponding to the first collimation width.

In 840, the acquisition unit 610 may obtain image data related to a scanning at a target collimation width. The image data may be obtained from other component in the CT system 100, such as the storage device 150 or the storage module 430. The image data may be associated with the radiations that pass through or be scattered by a scanned object in the scanning with the target collimation width.

In 850, the correction coefficient determination unit 630 may determine a target correction coefficient corresponding to the target collimation width based on the target collimation width, and the relationship between correction coefficients and collimation widths. As described in connection with operation 830, the relationship between collimation widths and radiation intensities may be described according to Equation (4). The target correction coefficient may be determined based on the target collimation width and the Equation (4).

In 860, the correction unit 640 may modify the image data based on the target correction coefficient. In some embodiments, the correction unit 640 may modify the image data by multiplying the image data with the target correction coefficient. For example, the image data may include projection data related to the scanning. For illustration purpose, assuming that the correction coefficient is equal to eight, the correction unit 640 may obtain modified projection data that is equal to eight times of the projection data.

It should be noted that the above descriptions of process 800 are provided for the purposes of illustration, and not intended to limit the scope of the present disclosure. For persons having ordinary skills in the art, various modifications and changes in the forms and details of the application of the above method and system may occur without departing from the principles of the present disclosure. However, those variations and modifications also fall within the scope of the present disclosure.

In some embodiments, the order of the operations in process 800 may be changed. For example, 810 and 840 may be performed simultaneously. In some embodiments, the relationship between collimation widths and correction coefficients may be stored in a storage device (e.g., the storage device 150, the storage 220). The correction coefficient determination unit 630 may retrieve the relationship (e.g., a look-up table) from the storage device and determine a correction coefficient corresponding to a collimation width based on the retrieved relationship. For example, a table of collimation widths and their corresponding correction coefficients may be stored in the storage device. The correction coefficient determination unit 630 may determine the correction coefficient corresponding to the collimation width by looking up the table.

In some embodiments, in 820, the relationship determination unit 620 may obtain a relationship between collimation widths and ratios of scattered radiation intensities over the primary radiation intensity. In 830, the relationship determination unit 620 may determine the relationship between correction coefficients and collimation widths based on the first correction coefficient, the first collimation width, and the relationship between relationship between collimation widths and ratios of scattered radiation intensities over the primary radiation intensity. The relationship determination unit 620 may designate the relationship between collimation widths and ratios of scattered radiation intensities over the primary radiation intensity of the second object as the relationship between scattered radiation intensities and collimation widths. More descriptions regarding the determinations of the relationship between collimation widths and ratios of scattered radiation intensities over the primary radiation intensity may be found elsewhere in the present disclosure (e.g., FIG. 10 and the relevant descriptions).

Figure 9:
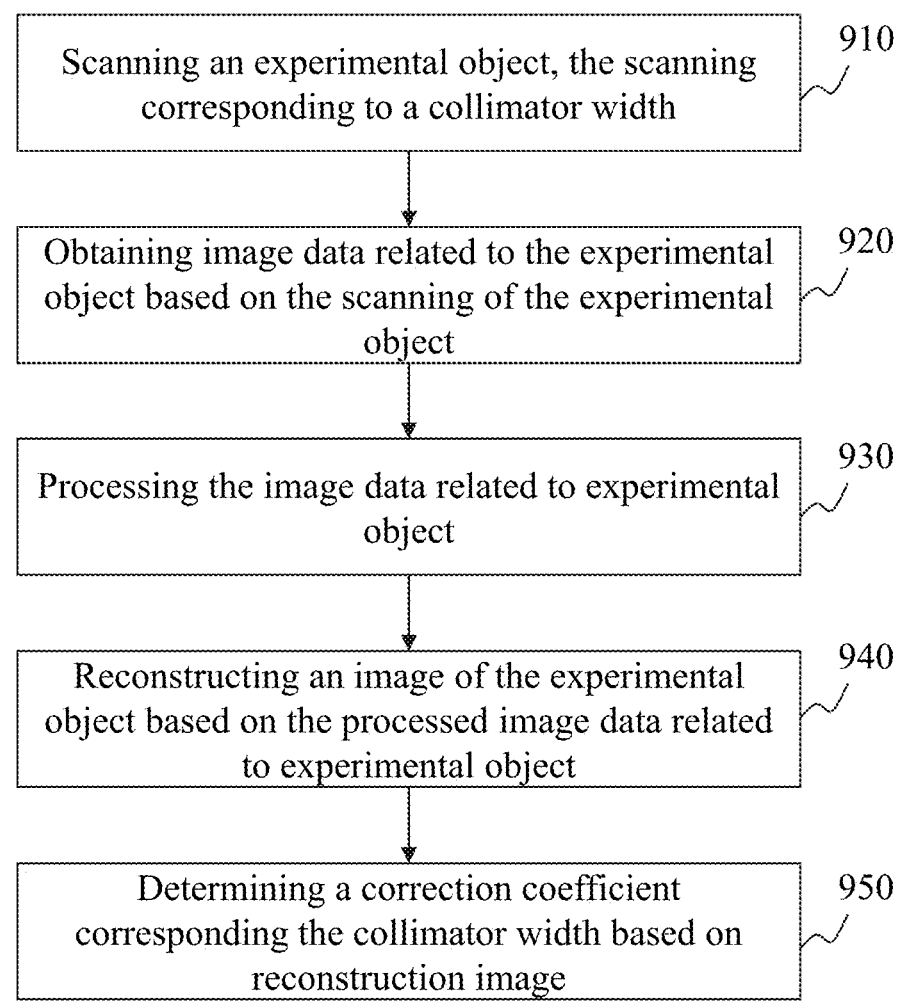
FIG. 9 is a flowchart illustrating an exemplary process for determining a correction coefficient corresponding to a collimation width according to some embodiments of the present disclosure.

FIG. 9 illustrates a flowchart illustrating an exemplary process for determining a correction coefficient corresponding to a collimation width according to some embodiments of the present disclosure. In some embodiments, at least part of the process 900 may be performed by the processing device 140 (implemented in, for example, the computing device 200 shown in FIG. 2). In some embodiments, operation 810 of the process 800 may be performed according to one or more operations in the process 900.

In 910, the CT scanner 110 may scan an experimental object with a collimation width. The collimation width may be 1 mm, 2 mm, 10 mm, 20 mm, 40 mm or any suitable other number. More descriptions regarding the collimation width may be found elsewhere in the present disclosure (e.g., FIGS. 4A and 7 and the relevant descriptions). In some embodiments, the experimental object may be a water phantom. The diameter of the water phantom may be 100 mm, 180 mm, 200 mm, or any other suitable number. The thickness of a wall of the water phantom may be 1 mm, 2 mm, 3 mm, or any other suitable number.

In 920, the acquisition module 510 may obtain image data related to the experimental object based on the scanning of the experimental object. The image data may be associated with radiations that pass through or be scattered by the object. More descriptions regarding the image data may be found elsewhere in the present disclosure (e.g., FIG. 7 and the relevant descriptions).

In 930, the processing device 140 may process the obtained image data. The image data processing may include one or more data processing operations, such as data projection, data filtering, data sequencing, data modifying. In some embodiments, the processing device 140 may modify the image data related to the experimental object by removing noise (e.g., a gain inhomogeneity, an intensity inhomogeneity, or an artifact).

In 940, the processing device 140 may reconstruct an image of the experimental object based on the processed image data. The reconstructed image may be a 3D image, 4D image data, a 4D image, or the like, or any combination thereof. The processing module 540 may reconstruct the image based on the image data according to a reconstruction algorithm. More descriptions regarding the generation of the reconstructed image may be found elsewhere in the present disclosure (e.g., FIG. 7 and the relevant descriptions).

In 950, the correction coefficient determination unit 630 may determine a correction coefficient corresponding to the collimation width based on the reconstructed image. For example, the experimental object may be a water phantom, and the correction coefficient determination unit 630 may obtain a sub-area of the reconstructed image of the water phantom. The correction coefficient determination unit 630 may determine the correction coefficient based on pixel values of the pixels in the subarea. The subarea may correspond to any part of the water phantom in the reconstructed image. Merely by way of example, the subarea may correspond to a central area of the water phantom. The subarea may have any regular shape (e.g., a circle, a rectangle, or a square) or any irregular shape. In some embodiments, the correction coefficient determination unit 630 may determine a $\mu_{water}$ based on an average pixel value of the pixels in the subarea. The correction coefficient determination unit 630 may then determine the correction coefficient corresponding to the collimation width based on the $\mu_{water}$ according to Equation (2) as described elsewhere in this disclosure (e.g., FIG. 7 and the relevant descriptions). For illustration purpose, assuming that the $\mu_{water}$ is equal to 125 HU, the correction coefficient corresponding to the collimation width may be determined by dividing 1000 by 125 and be equal to 8.

It should be noted that the above descriptions of process 900 are provided for the purposes of illustration, and not intended to limit the scope of the present disclosure. For persons having ordinary skills in the art, various modifications and changes in the forms and details of the application of the above method and system may occur without departing from the principles of the present disclosure. In some embodiments, one or more operations may be added or omitted. For example, additional operations may be performed before 910 to scan air and obtain image data related to the air based on the scanning of the air. The scanning of air may be performed by the CT scanner 110 with a collimation width that is same with the collimation width in 910. In 930, the processing device 140 may modify the image data related to experimental object based on the image data related to the air to remove noise caused by the air. In some embodiments, the CT scanner 110 may perform the scanning of the experimental object or the air under an instruction of the processing device 140 (e.g., an instruction sent by the control module 520). However, those variations and modifications also fall within the scope of the present disclosure.

Figure 10:
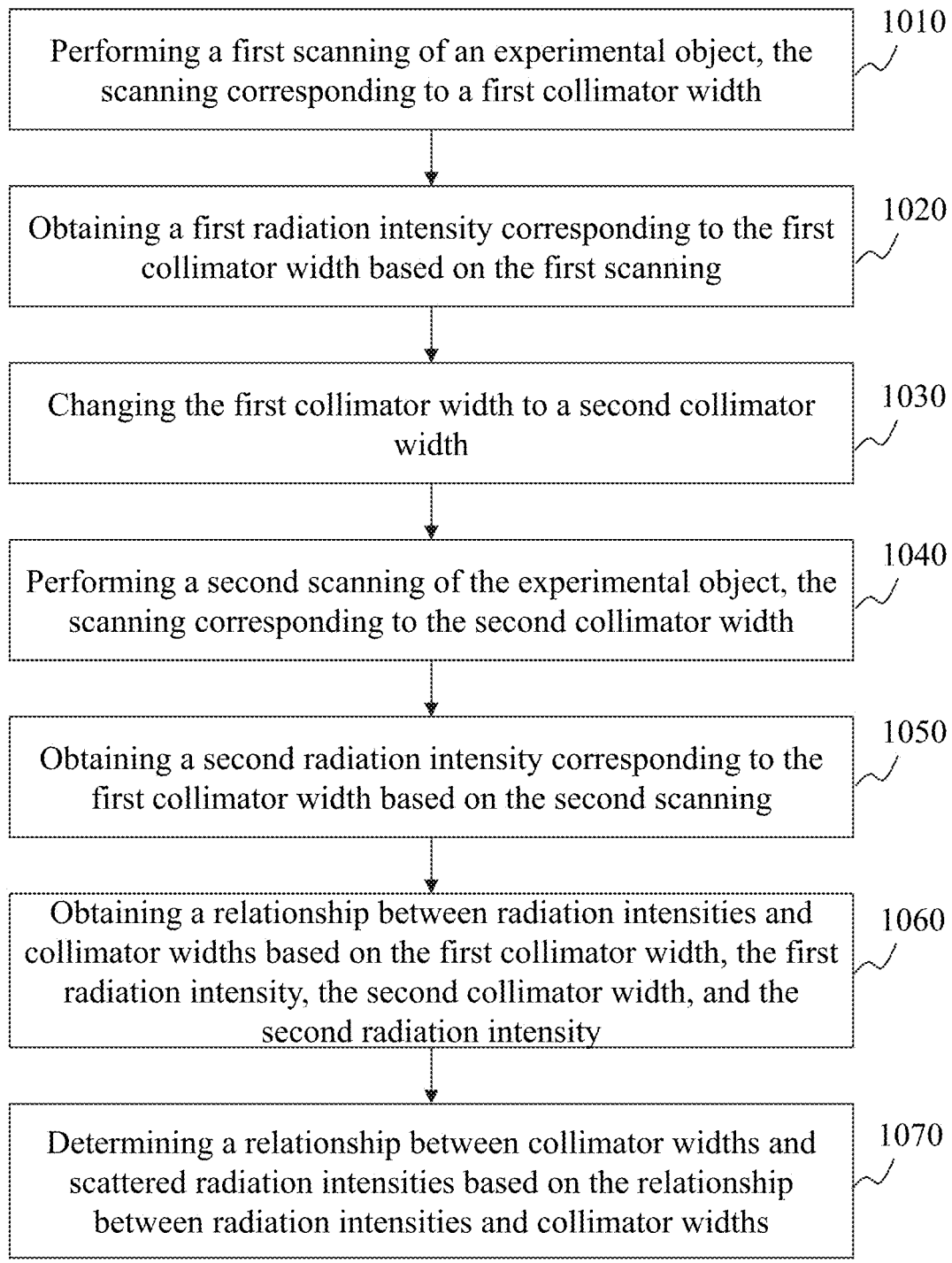
FIG. 10 is a flowchart illustrating an exemplary process for determining the relationship between collimation widths and scattered radiation intensities according to some embodiments of the present disclosure.

FIG. 10 illustrates a flowchart illustrating an exemplary process for determining the relationship between collimation widths and scattered radiation intensities according to some embodiments of the present disclosure. In some embodiments, at least part of the process 1000 may be performed by the processing device 140 (implemented in, for example, the computing device 200 shown in FIG. 2). In some embodiments, operation 820 of the process 800 may be performed according to one or more operations in the process 1000.

In 1010, the CT scanner 110 may perform a first scanning by scanning an experimental object with a first collimation width. In some embodiments, the experimental object may be a water phantom. More descriptions regarding the collimation width and the experimental object may be found elsewhere in the present disclosure (e.g., FIG. 9 and the relevant descriptions).

In 1020, the relationship determination unit 620 may obtain a first radiation intensity corresponding to the first collimation width based on the first scanning. In some embodiments, the acquisition module 510 may obtain image data related to the object based on the first scanning. The image data of the first scanning may be associated with the radiations that pass through or be scattered by the experimental object. The relationship determination unit 620 may determine a first radiation intensity corresponding to the first collimation width based on the image data of the first scanning.

In 1030, the CT scanner 110 may change the first collimation width to a second collimation width. In some embodiments, the control module 520 may instruct the CT scanner 110 to change the collimation width from the first collimation width to the second collimation width.

In 1040, the CT scanner 110 may perform a second scanning by scanning the experimental object with the second collimation width.

In 1050, the relationship determination unit 620 may obtain a second radiation intensity corresponding to the second collimation width based on the second scanning. Step 1050 may be similar to step 1020 described above, and thus the description thereof will not be repeated here.

In 1060, the relationship determination unit 620 may obtain a relationship between radiation intensities and collimation widths based on the first collimation width, the first radiation intensity, the second collimation width, and the second radiation intensity. The relationship be may be recorded in the form of a table, a drawing, a mathematical expression, etc. For example, the relationship determination unit 620 may record the first collimation width and the corresponding first radiation intensity, the second collimation width and the corresponding second radiation intensity in a table and transmit the table to a storage device (e.g., the storage module 530). As another example, the relationship determination unit 620 may determine a mathematical function based on the first collimation width and the corresponding first radiation intensity, the second collimation width and the corresponding second radiation intensity. In some embodiments, the mathematical function may be a linear function with the collimation width being an independent variable and the radiation intensity being a dependent variable. In some embodiments, the relationship determination unit 620 may determine a mathematical function according to a curve fitting technique.

In 1070, the relationship determination unit 620 may determine a relationship between collimation widths and scattered radiation intensities based on the relationship between collimation widths and radiation intensities. For illustration purpose, the relationship between collimation widths and radiation intensities as described in connection with operation 1060 may be described according to Equation (6) below:

$$I=f(w) \qquad \text{Equation (6),}$$

where I refers to the radiation intensity, and w refers to the collimation width.

The radiation intensity may be equal to a sum of a scattered radiation intensity and a primary radiation intensity. The primary radiation intensity of the experimental object may be constant, and the scattered radiation intensity may be associated with the collimation width as described elsewhere in this disclosure (e.g., FIGS. 4A and 4B and the relevant descriptions). When the collimation width is close to zero, the scatter radiation intensity may be close to zero and the radiation intensity may be roughly equal to the primary radiation intensity. As used herein, "being roughly equal to" may indicate that the difference between the radiation intensity and the primary radiation intensity is at most 0.01%, 0.1%, 1%, 2% or any other values of the radiation intensity. The relationship between collimation widths and scattered radiation intensities may be determined based on Equation (6) and be described according to Equation (7) below:

$$S=f(w)-f(w_0) \qquad \text{Equation (7),}$$

where S refers to the scattered radiation intensity, $w_0$ refers to the collimation width being equal to zero, and $f(w_0)$ refers to the primary radiation of the experimental object.

It should be noted that the above descriptions of process 1000 are provided for the purposes of illustration, and not intended to limit the scope of the present disclosure. For persons having ordinary skills in the art, various modifications and changes in the forms and details of the application of the above method and system may occur without departing from the principles of the present disclosure. However, those variations and modifications also fall within the scope of the present disclosure.

In some embodiments, operations 1030 to 1050 may be performed for multiple times to obtain multiple radiation intensities corresponding to multiple collimation widths. In 1060, the relationship determination unit 620 may obtain the relationship between collimation widths and radiation intensities based on the first collimation width, the first radiation intensity, and the multiple collimation widths and their corresponding radiation intensities. The determination of the relationship between collimation widths and radiation intensities may be performed according on a curve fitting technique. For example, a mathematical function recording the relationship between collimation widths and radiation intensities may be determined based on the first collimation width, the first radiation intensity, and the multiple collimation widths and their corresponding radiation intensities according to the curve fitting technique. The mathematical function may include but is not limited to a linear function, an inverse function, an inverse function as described elsewhere in this disclosure (e.g., FIG. 8 and the relevant descriptions).

In some embodiments, an additional operation may be performed to determine the relationship between relationship between collimation widths and ratios of scattered radiation intensities over the primary radiation intensity as described elsewhere in this disclosure (e.g., FIG. 8 and the relevant descriptions). The relationship between collimation widths and scattered radiation intensities may be determined based on Equation (7) and be described according to Equation (8) below:

$$S=f(R*f(w_0))-f(w_0) \qquad \text{Equation (8),}$$

where S refers to the scattered radiation intensity, $w_0$ refers to the collimation width being equal to zero, $f(w_0)$ refers to the primary radiation of the experimental object, and R refers to the ratio of scattered radiation intensity over the primary radiation intensity.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C #, VB. NET, Python or the like, conventional procedural programming languages, such as the "C" programming language, Visual Basic, Fortran 2103, Perl, COBOL 2102, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, for example, an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed subject matter requires more features than are expressly recited in each claim. Rather, inventive embodiments lie in less than all features of a single foregoing disclosed embodiment.

In some embodiments, the numbers expressing quantities or properties used to describe and claim certain embodiments of the application are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

I claim:

1. A system, comprising:
a scanner having a collimator, a collimation width of the collimator being adjustable;
one or more non-transitory storage devices including a set of instructions for image data processing; and
at least one processor configured to communicate with the one or more non-transitory storage devices, wherein when executing the set of instructions, the at least one processor is configured to cause the system to:
obtain image data of a first object, the image data relating to a scanning of the first object with a first collimation width of the collimator;
determine, based on the image data, a first correction coefficient corresponding to the first collimation width of the collimator;
obtain a relationship between scattered radiation intensities and collimation widths; and
determine a relationship between correction coefficients and collimation widths based on the first correction coefficient, the first collimation width, and the relationship between scattered radiation intensities and collimation widths.

2. The system of claim 1, wherein the at least one processor is configured to cause the system to:
obtain a target collimation width of the collimator and target image data related to a scanning with the target collimation width;
determine a target correction coefficient based on the target collimation width and the relationship between correction coefficients and collimation widths; and
modify the target image data based on the target correction coefficient.

3. The system of claim 1, wherein the at least one processor is further configured to cause the system to save the determined relationship between correction coefficients and collimation widths to the one or more non-transitory storage devices.

4. The system of claim 1, wherein to determine the first correction coefficient corresponding to the first collimation width, the at least one processor is configured to cause the system to:
instruct the scanner to scan the first object with the first collimation width;
obtain the image data related to the first object based on the scanning of the first object;
process the image data related to the first object;
reconstruct an image of the first object based on the processed image data related to the first object; and
determine the first correction coefficient corresponding to the first collimation width based on the reconstructed image of the first object.

5. The system of claim 4, wherein the first object is a water phantom.

6. The system of claim 4, wherein to instruct the scanner to scan the first object with the first collimation width, the at least one processor is configured to cause the system to:
instruct the scanner to scan air with the first collimation width.

7. The system of claim 1, wherein to obtain the relationship between scattered radiation intensities and collimation widths, the at least one processor is configured to cause the system to:
instruct the scanner to perform a first scanning of a second object with a second collimation width;
obtain a first radiation intensity based on the first scanning of the second object;
instruct the scanner to change the collimation width from the second collimation width to a third collimation width;
instruct the scanner to perform a second scanning of the second object with the third collimation width;
obtain a second radiation intensity based on the second scanning of the second object;
determine the relationship between radiation intensities and collimation widths based on the second collimation width, the first radiation intensity, the third collimation width, and the second radiation intensity; and
determine the relationship between scattered radiation intensities and collimation widths based on the determined relationship between radiation intensities and collimation widths.

8. The system of claim 7, wherein the determination of the relationship between radiation intensities and collimation widths based on the second collimation width, the first radiation intensity, the third collimation width, and the second radiation intensity is performed according to a curve fitting technique.

9. The system of claim 7, wherein to determine the relationship between scattered radiation intensities and collimation widths based on the relationship between radiation intensities and collimation widths, the at least one processor is configured to cause the system to:
determine a primary radiation intensity of the second object based on the relationship between radiation intensities and collimation widths.

10. The system of claim 9, wherein to determine the relationship between scattered radiation intensities and collimation widths, the at least one processor is configured to cause the system to:
obtain a relationship between collimation widths and ratios of scattered radiation intensities over the primary radiation intensity of the second object; and
designate the relationship between collimation widths and ratios of scattered radiation intensities over the primary radiation intensity of the second object as the relationship between scattered radiation intensities and collimation widths.

11. A computer-implemented method for image data processing, the method comprising the following operations performed by at least one processor:
obtaining, by the at least one processor, image data of a first object, the image data relating to a scanning of the first object with a first collimation width of a collimator;
determining, by the at least one processor, based on the image data, a first correction coefficient corresponding to the first collimation width of the collimator;
obtaining, by the at least one processor, a relationship between scattered radiation intensities and collimation widths; and
determining, by the at least one processor, a relationship between correction coefficients and collimation widths based on the first correction coefficient, the first collimation width, and the relationship between scattered radiation intensities and collimation widths.

12. The method of claim 11, further comprising:
obtaining a target collimation width of the collimator and target image data related to a scanning with the target collimation width;

determining a target correction coefficient based on the target collimation width and the relationship between correction coefficients and collimation widths; and modifying the target image data based on the target correction coefficient.

13. The method of claim 11, wherein the determining the first correction coefficient corresponding to the first collimation width further comprises:

instructing, by the at least one processor, a scanner to scan the first object with the first collimation width;

obtaining, by the at least one processor, the image data related to the first object based on the scanning of the first object;

processing, by the at least one processor, the image data related to the first object;

reconstructing, by the at least one processor, an image of the first object based on the processed image data related to the first object; and determining, by the at least one processor, the first correction coefficient corresponding to the first collimation width based on the reconstructed image of the first object.

14. The method of claim 12, wherein obtaining the relationship between scattered radiation intensities and collimation widths further comprises:

instructing, by the at least one processor, a scanner to perform a first scanning of a second object with a second collimation width;

obtaining, by the at least one processor, a first radiation intensity based on the first scanning of the second object;

instructing, by the at least one processor, the scanner to change from the second collimation width to a third collimation width;

instructing, by the at least one processor, the scanner to perform a second scanning of the second object with the third collimation width;

obtaining, by the at least one processor, a second radiation intensity based on the second scanning of the second object;

determining, by the at least one processor, the relationship between radiation intensities and collimation widths based on the second collimation width, the first radiation intensity, the third collimation width, and the second radiation intensity; and determining, by the at least one processor, the relationship between scattered radiation intensities and collimation widths based on the determined relationship between radiation intensities and collimation widths.

15. The method of claim 14, wherein determining the relationship between radiation intensities and collimation widths based on the second collimation width, the first radiation intensity, the third collimation width, and the second radiation intensity is performed according to a curve fitting technique.

16. The method of claim 15, wherein determining the relationship between scattered radiation intensities and collimation widths further comprises:

obtaining, by the at least one processor, a relationship between collimation widths and ratios of scattered radiation intensities over the primary radiation intensity of the second object; and designate the relationship between collimation widths and ratios of scattered radiation intensities over the primary radiation intensity of the second object as the relationship between scattered radiation intensities and collimation widths.

17. The method of claim 14, wherein determining the relationship between scattered radiation intensities and collimation widths based on the relationship between radiation intensities and collimation widths further comprises:

determining, by the at least one processor, a primary radiation intensity of the second object based on the relationship between radiation intensities and collimation widths.

18. A non-transitory computer-readable storage medium including instructions that, when accessed by at least one processor of a system, cause the system to:

obtain image data of a first object, the image data relating to a scanning of the first object with a first collimation width of a collimator;

determine, based on the image data, a first correction coefficient corresponding to the first collimation width of the collimator;

obtain a relationship between scattered radiation intensities and collimation widths; and determine a relationship between correction coefficients and collimation widths based on the first correction coefficient, the first collimation width, and the relationship between scattered radiation intensities and collimation widths.

19. The non-transitory computer-readable storage medium of claim 18, wherein the instructions further causes the system to:

obtain a target collimation width of the collimator and target image data related to a scanning with the target collimation width;

determine a target correction coefficient based on the target collimation width and the relationship between correction coefficients and collimation widths; and modify the target image data based on the target correction coefficient.

20. The non-transitory computer-readable storage medium of claim 18, wherein to obtain the relationship between scattered radiation intensities and collimation widths, the instructions further causes the system to:

instruct a scanner to perform a first scanning of a second object with a second collimation width;

obtain a first radiation intensity based on the first scanning of the second object;

instruct the scanner to change the collimation width from the second collimation width to a third collimation width;

instruct the scanner to perform a second scanning of the second object with the third collimation width;

obtain a second radiation intensity based on the second scanning of the second object;

determine the relationship between radiation intensities and collimation widths based on the second collimation width, the first radiation intensity, the third collimation width, and the second radiation intensity; and determine the relationship between scattered radiation intensities and collimation widths based on the determined relationship between radiation intensities and collimation widths.

* * * * *